United States Patent
Borody

(10) Patent No.: US 9,050,358 B2
(45) Date of Patent: *Jun. 9, 2015

(54) COMPOSITIONS AND METHODS FOR PROBIOTIC RECOLONIZATION THERAPIES

(71) Applicant: Thomas Julius Borody, Five Dock (AU)

(72) Inventor: Thomas Julius Borody, Five Dock (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,034

(22) Filed: May 5, 2014

(65) Prior Publication Data

US 2014/0234260 A1 Aug. 21, 2014

Related U.S. Application Data

(60) Continuation of application No. 13/910,579, filed on Jun. 5, 2013, which is a division of application No. 10/332,986, filed on Aug. 4, 2003, now Pat. No. 8,460,648, and a division of application No. 10/332,986, filed as application No. PCT/AU01/00907 on Jul. 25, 2001, now Pat. No. 8,460,648.

(30) Foreign Application Priority Data

Jul. 25, 2000 (AU) ........................ PQ8997

(51) Int. Cl.

| | | |
|---|---|---|
| *A61K 39/08* | (2006.01) | |
| *A61K 39/00* | (2006.01) | |
| *A61K 39/38* | (2006.01) | |
| *A61K 39/116* | (2006.01) | |
| *A61K 39/09* | (2006.01) | |
| *A01N 63/00* | (2006.01) | |
| *A01N 65/00* | (2009.01) | |
| *A61K 38/48* | (2006.01) | |
| *A23L 1/30* | (2006.01) | |
| *A61K 36/062* | (2006.01) | |
| *A61K 45/06* | (2006.01) | |
| *A61K 38/14* | (2006.01) | |
| *A61K 31/341* | (2006.01) | |
| *A61K 31/41* | (2006.01) | |
| *A61K 31/495* | (2006.01) | |
| *A61K 31/7034* | (2006.01) | |
| *A23L 2/52* | (2006.01) | |
| *A61K 35/74* | (2006.01) | |

(52) U.S. Cl.
CPC .............. *A61K 35/741* (2013.01); *A61K 35/74* (2013.01); *A61K 38/4893* (2013.01); *A23L 1/3014* (2013.01); *A61K 35/742* (2013.01); *A61K 35/744* (2013.01); *A61K 35/747* (2013.01); *A61K 36/062* (2013.01); *A61K 45/06* (2013.01); *A61K 38/14* (2013.01); *A61K 31/341* (2013.01); *A61K 31/41* (2013.01); *A61K 31/495* (2013.01); *A61K 31/7034* (2013.01); *A23L 2/52* (2013.01); *A61K 35/745* (2013.01)

(58) Field of Classification Search
CPC .................................................. A61K 38/4893
See application file for complete search history.

(56) References Cited

U.S. PATENT DOCUMENTS

| | | |
|---|---|---|
| 4,710,379 A | 12/1987 | Kawai et al. |
| 4,892,731 A | 1/1990 | Arai |
| 5,266,315 A | 11/1993 | Taguchi et al. |
| 5,443,826 A * | 8/1995 | Borody ...................... 424/93.3 |
| 5,728,380 A | 3/1998 | Allen et al. |
| 5,800,821 A * | 9/1998 | Acheson et al. ........... 424/200.1 |
| 5,837,238 A | 11/1998 | Casas et al. |
| 5,858,356 A | 1/1999 | Wolf et al. |
| 5,902,578 A | 5/1999 | Halpin-Dohnalek et al. |
| 5,902,743 A | 5/1999 | Luchansky et al. |
| 6,645,530 B1 | 11/2003 | Borody |

(Continued)

FOREIGN PATENT DOCUMENTS

| | | |
|---|---|---|
| CA | 1333564 | 12/1994 |
| EP | 0433299 B1 | 6/1991 |

(Continued)

OTHER PUBLICATIONS

WebMDHealth (http://mywebmd.com/hw/inflammatory_bowel/uf6012.asp, pp. 1-2), accessed Oct. 23, 2005.

(Continued)

*Primary Examiner* — Gary Nickol
*Assistant Examiner* — Lakia Tongue
(74) *Attorney, Agent, or Firm* — Gregory P. Einhorn; Greer Burns & Crain Ltd.

(57) ABSTRACT

The present invention relates to pharmaceutical compositions suitable for the treatment of chronic diseases associated with the presence of abnormal or an abnormal distribution of microflora in the gastrointestinal tract of a mammalian host, which compositions comprise viable non-pathogenic or attenuated pathogenic *Clostridia*. The compositions further comprise one or more additional viable non-pathogenic or attenuated pathogenic microorganisms selected from the group consisting of *Bacteroides*, Eubacteria, Fusobacteria, Propionibacteria, *Lactobacilli*, anaerobic cocci, *Ruminococcus, E. coli, Gemmiger, Desulfomonas, Peptostreptococcus*, and fungi. The present invention also provides pharmaceutical compositions suitable for the treatment of the same chronic diseases comprising viable non-pathogenic or attenuated pathogenic *Escherichia coli*, at least one strain of viable non-pathogenic or attenuated pathogenic *Bacteroides* and at least one strain of viable non-pathogenic or attenuated pathogenic microorganism.

19 Claims, No Drawings

(56) References Cited

U.S. PATENT DOCUMENTS

| | | | |
|---|---|---|---|
| 7,374,753 B1* | 5/2008 | Farmer et al. | 424/93.46 |
| 8,460,648 B2* | 6/2013 | Borody | 424/93.3 |
| 2001/0014322 A1* | 8/2001 | Chen et al. | 424/93.45 |
| 2002/0013270 A1* | 1/2002 | Bolte | 514/8 |
| 2002/0022019 A1 | 2/2002 | Laulund | |
| 2004/0062757 A1 | 4/2004 | Finegold | |
| 2004/0170617 A1 | 9/2004 | Finegold | |
| 2006/0099197 A1* | 5/2006 | Farmer | 424/93.46 |

FOREIGN PATENT DOCUMENTS

| | | |
|---|---|---|
| EP | 0456418 | 11/1991 |
| JP | 07-242557 | 9/1995 |
| WO | 90/01335 | 2/1990 |
| WO | 96/11014 | 4/1996 |
| WO | 98/13068 | 4/1998 |
| WO | 00/07571 | 2/2000 |
| WO | 00/42168 | 7/2000 |

OTHER PUBLICATIONS

InteliHealth (http://www.intelihealth.com, pp. 1-4), accessed Oct. 23, 2005.

Multiple authors (Cure Autism Now: 2004 Funding cycle, www.cureautismnow.org), pp. 1-7).

Health A to Z (www.healthatoz.com, pp. 1-7), accessed Oct. 23, 2005.

HealingWithNutrition.com (http://www.HealingWith Nutrition.com/disease/inflambowels/chrohns.html, pp. 1-4), accessed Oct. 23, 2005.

Health Encyclopedia—Autism (www.healthscout.com, pp. 1-5), accessed Nov. 22, 2005.

Madsen, The use of probiotics in gastrointestinal disease, Can J. Gastroenterol, 2001: 15(12): 817-22).

Andrews, "Putting back the bugs": bacterial treatment relieves chronic constipation and symptoms of irritable bowel syndrome, Med. J. Aug. 1993: 159(9): 633-4).

Stedman's Medical Dictionary—definition of Monilia, accessed Nov. 22, 2005.

Encarta—definition of probiotic, accessed Dec. 1, 2005.

Martin H. Floch and Khalid Moussa, "Probiotics and Dietary Fiber, The Clinical Coming of Age of Intestinal Microecology," J. Clin. Gastroenterology, Lippincott Williams & Wilkins (Philadelphia), vol. 27 (No. 2), pp. 99-100.

E.R. Bolte, "Autism and Clostridium tetani," Medical Hypotheses, Harcourt Brace & Co., Ltd., p. 133-144, (1998).

S.P. Boriello, "Clostridial Disease of the Gut," Clinical Infectious Diseases, The University of Chicago, vol. 20 (No. Sup), p. S242-S250, (1995).

B. Hensel, U.C. Seib and H.H. Wellhoner, "Vagal Ascent and Distribution of 125 I-Tetanus Toxin after Injection into the Anterior Wall of the Stomach," Naunyn-Schmiedeberg's Arch. Pharmacol, Springer-Verlag, p. 395-402 (1973).

Sandler et al, "Possible Gut-Brain Interaction Contributing to Delayed Onset Autism Symptomatology," Fourth Int. Symp. Brain-Gut Interactions, Blackwell Science Ltd., vol. 10 (No. 4), p. 33, (Aug. 1998).

George F. Longstreth, "Irritable Bowel Syndrome: A Multibillion-Dollar Problem," Gastroenterology, The American Gastroenterological Association, p. 2029-2031 (1995).

G. Zoppi et al., "The Intestinal Ecosystem in Chronic Functional Constipation," ACTA Paediatr, Scandinavian University Press, p. 836-841 (1998).

K. Irrgang and U. Sonnenborn, "The Historical Development of Mutaflor Therapy," Ardeypharm GmbH, Herdecke, Loerfeldstrabe 20, Germany, p. 38, pgs., (1998).

Mutaflor Brief Summary of Therapeutic Principles Ardeypharm GmbH 0796 D-58313 Herdecke Germany 6 pgs.

Mutaflor Safety of Therapy, Ardeypharm GmbH 0796, D-58313 Herdecke Germany, 4 pgs, Jan. 1988.

Mutaflor for Functional and Inflammatory Bowel Diseases for Extraintestinal Manifestations for Activtion of the Body's In-Built Defences, Ardeypharam GmbH 0796, D-58313 Herdecke Germany, 8 pgs, faxed Jun. 15, 2006.

Derwent Abstract Accession No. 98-230427/20, WO 98/13068 A, (Kuperman VB) Apr. 2, 1998, Abstract.

* cited by examiner

COMPOSITIONS AND METHODS FOR PROBIOTIC RECOLONIZATION THERAPIES

CROSS-REFERENCE TO RELATED APPLICATIONS

This United States utility patent application is a continuation of U.S. Ser. No. 13/910,579, filed Jun. 5, 2013, which is a divisional of U.S. Ser. No. 10/332,986, filed Aug. 4, 2003, now U.S. Pat. No. 8,460,648, issued Jun. 11, 2013 which is a §371 national phase of PCT international patent application no. PCT/AU01/00907, having an international filing date of Jul. 25, 2001, which claims benefit of priority to Australian Patent Application Serial No. PQ 8997, filed Jul. 25, 2000. The aforementioned applications are expressly incorporated herein by reference in their entirety and for all purposes.

TECHNICAL FIELD

The present invention relates to pharmaceutical compositions suitable for the treatment of diseases in mammals, in particular to the treatment of chronic disorders associated with the presence of abnormal or an abnormal distribution of microflora in the gastrointestinal tract. The invention also relates to methods of treating such diseases.

BACKGROUND ART

There are large numbers of patients suffering from gastro-intestinal symptoms referable to the lower small bowel and large bowel which to date have eluded explanation, These disorders include irritable bowel syndrome (IBS) or spastic colon, idiopathic ulcerative colitis, mucous colitis, collagenous colitis, Crohn's disease, inflammatory bowel disease in general, microscopic colitis, antibiotic-associated colitis, idiopathic or simple constipation, diverticular disease, and AIDS enteropathy. Pathophysiology of these disorders eludes logical explanation in spite of decades of research and millions of dollars of research funds. A common underlying factor shared by all these disorders observed by the present inventor is their onset or aggravation following some extraneous invading infection e.g., traveler's diarrhea. In all the disorders, a specific causal infection generally cannot be demonstrated due to our inability to detect infecting agents whose cultural characteristics are unknown to medical science.

Circumstantial evidence which suggests that these disorders are "infection-related" includes: (a) onset following a gastro-intestinal infection which failed to completely resolve; (b) transient improvement with use of certain antibiotics, but recurrence upon cessation of antibiotics; (c) transient improvement following orthostatic lavage prior to colonoscopy and; (d) transient symptom improvement with use of "colonic" irrigation.

It is impractical to use long-term antibiotic therapy (with its associated complications) in such patients since cure is not obtained with its use. Furthermore, chronic gut infections with recognized, specific pathogens such as *Clostridium difficile, Yersinia enterocolitica* or *Campylobacter jejuni/coli* are generally not eradicated with antibiotics. Some previous attempts have been made to alter the enteric microflora in order to eradicate such chronic infections. These measures nevertheless indicate that alteration of bacterial flora may effect dramatic clinical improvement in conditions characterized by chronic, resistant enterocolitic infection. However there remain many chronic disorders of uncertain aetiology or causation, which are resistant to cure by current therapeutic techniques.

The use of probiotics in the human population has been largely confined to. the inclusion in various foods of live organism of *Lactobacilli* and *Bifidobacteria* and less frequently *Streptococcus faecalis* or several strains of *Escherichia coli*. These organisms are thought to promote health via immune stimulation and reconstitution of what is presumed to be normal flora. Such usage stems back to the beliefs generated by Mechnikov in the early 1900s. The use of probiotics to treat established infections in the gastrointestinal tract has been lesser but a growing part of the use of probiotics. Fungal agents such as *Saccharomyces boulardii* have been used to treat, albeit inefficiently, *Clostridium difficile* infection and *Lactobacillus* GG has also been used for this purpose (Floch M. Probiotics and Dietary Fibre. J Clin Gastroenterol 1998; 27(2):99-100). Various patents have claimed the use of probiotics for narrow disease conditions including treatment of *Clostridium difficile* with a combination of Vancomycin and butyric acid bacteria (U.S. Pat. No. 5,266,315), diarrhea prevention using *Lactobacillus* (U.S. Pat. No. 5,837, 238) or *Bifidobacterium* (U.S. Pat. No. 5,902,743), *Lactobacillus acidophilus* to inhibit cryptosporidium (U.S. Pat. No. 5,858,356) and mixtures of *Lactobacilli* and Bifidobacteria in infants to prevent diarrhea. *Enterococcus faecium* has been claimed to be useful in alleviating symptoms of Irritable Bowel Syndrome in humans (U.S. Pat. No. 5,902,578) (U.S. Pat. No. 5,728,380) but this has not recognized *Clostridium* as the underlying agent in this condition. *Clostridium butyricum* as a single agent has been claimed to be a biological intestinal antiseptic for treatment of bacterial food poisonings (U.S. Pat. No. 4,892,731), but its use in chronic disease treatment was not contemplated.

Previous attempts to alter the enteric microflora of a patient have prescribed the removal of at least a part of the host's existing enteric microflora, for instance by lavage, prior to substitution with predetermined desired microflora. This procedure, which was the preferred embodiment of WO90/01335 has the distinct disadvantages of complicating the treatment and of causing further discomfort to the patient. This patent also advocated the use of dried, reconstituted faeces or a synthetic mixture comprising *Bacteroides* sp. and *Escherichia coli*. It has now been surprisingly found that lavage or other methods of removal of at least a part of the host's existing enteric microflora can be omitted provided a non-pathogenic *Clostridium* sp. is included within the probiotic replacement mixture. Such a replacement mixture has the dual ability of displacing pathogenic bacteria, frequently Clostridial in nature and also establishing a normal environment in which commensal bacteria can establish. Such a treatment permits long-term recovery both from gastrointestinal disorders and from systemic afflictions not hitherto considered to be caused by harmful enteric flora. These are also called 'para-infective' phenomena and can include rheumatological, neurological, regressive, hepatic, and dermatological conditions among others.

Autism is a regressive disorder of childhood, affecting boys four times more often than girls. It has been observed that the onset of autism is often preceded by broad spectrum antibiotic use e.g. for recurrent ear infections. Antibiotic therapy is non-discriminatory in its action and apart from treating the ear infection the microflora of the healthy gastrointestinal tract can be severely disrupted by such treatment. This creates an environment where vulnerability to opportunistic microorganism colonization is heightened.

*Clostridium tetani* is a widely distributed, spore forming anaerobe. Toxigenic strains of *Clostridium tetani* produce the extremely potent tetanus neurotoxin which is known to enter the central nervous system from the intestinal tract via the vagus nerve (Hensel B et al. Naunyn Schmeidebergs Arch Pharmocol 1973; 276:395). Bolte (Med Hypotheses 1998; 51:133) has hypothesized that opportunistic infection by *Clostridium tetani* may be responsible for the behavioral and medical symptoms present in a sub-group of individuals diagnosed with autism. Others have also raised the possibility of *clostridia* in general as a cause of disease (Borriello S P. Clin Infect Dis 1995; Suppl 2:5242).

Sandier et al. (Fourth Int. Symp. Brain-Gut Interactions. 1998; 10: 363) report a trial in which children with delayed onset autism were treated with vancomycin over an 8 week period. All children in the trial had had antecedent broad-spectrum antibiotic exposure, followed by chronic persistent diarrhea and then onset of autistic features. Although significant post-treatment improvement was noted, all children eventually regressed towards baseline.

It is on the background of these known facts and later the results of trials of treatment, that the present invention was formulated. In brief, it was noted that autistic children (as well as related syndromes) who were referred for treatment of refractory 'irritable bowel syndrome' (IBS) viz diarrhea, flatulence, constipation, distension, abdominal pains etc— responded to treatment of their IBS when treated with a novel mix of probiotics. However, not only did their IBS improve dramatically but also their autistic features progressively regressed. Even after the initial 2-6 weeks of treatment eye contact was re-established, repetitive movements were much reduced, and word power (observed vocabulary) expanded— initially 20 words and ultimately >600 words at 12 months (estimated), creating ability of the autistic children to form long sentences. Continuing improvement was observed to occur over 12 months of treatment. These observations (to a lesser but definite degree at this stage of observations) also applied to those with Rett syndrome and children with Attention Deficit/Hyperactivity Disorder (ADHD), Attention Deficit Disorder (ADD), and autism variant Asperger's syndrome. The observations strongly suggest that the treatment of presumed enteric infection/s (e.g. Clostridial) in these conditions not only improves the IBS present but also the attendant neurological 'para-infective' phenomena called collectively autism, Asperger's, Rett syndrome, ADD or ADHD.

The inclusion within this specification of reference to published documents is not to be taken to be an admission that any one or more of those documents, nor the disclosure of any one or more of those documents, is part of the common general knowledge.

OBJECTS OF THE INVENTION

It is thus an object of the present invention to provide novel pharmaceutical compositions suitable for the treatment of various disease states related to the presence of 'abnormal' microflora in the gastrointestinal tract. It is a further object of the invention to propose the use of these pharmaceutical compositions in various disease states which have not previously been considered to owe their causation to the presence of abnormal flora in the gastrointestinal tract.

DISCLOSURE OF THE INVENTION

The present invention recognizes chronic infection/infestation as the underlying pathological process in a wide range of chronic disorders such as irritable bowel syndrome, particularly when characterized by chronic abdominal pain, bloating, or excessive flatulence, together with chronic diarrhea or alternating constipation/diarrhea, and also in spastic colon, mucous colitis, collagenous colitis, ulcerative colitis, Crohn's colitis, microscopic colitis, idiopathic inflammatory bowel disease, antibiotic-associated colitis, idiopathic or simple constipation, diverticular disease and AIDS enteropathy.

The invention has also been found to relate to other gastrointestinal disorders of unexplained aetiology such as polyposis coli and colonic polyps, which may well be influenced by the local bowel microflora.

In addition the present invention also provides a method of treatment of chronic gastrointestinal infections with specific microorganisms such as *Clostridium difficile, Yersinia* spp, *Campylobacter* spp, *Aeromonas* spp, *Escherichia coli, Cryptosporidium* spp, *Amoebae, Blastocystitis hominis, Giardia* and even chronic viral infections, and of small bowel bacterial overgrowth.

The present invention furthermore, recognizes the close association between the intestine and liver disease, and the intestine and migraines and chronic fatigue syndrome, and possibly other neurological syndromes such as, multiple sclerosis, amyotrophic lateral sclerosis, myasthenia gravis, Parkinson's disease, Alzheimer's disease, Chronic Inflammatory Demyelinating Polyneuropathy (CIDP), Guillain Barre Syndrome, and other degenerative disorders. Hence, it is proposed that a considerable proportion of currently unexplained diseases of the liver and nervous system of unknown aetiology may be explicable by the chronic growth of pathogens within the small/large intestine and the subsequent passage of antigenic material, pathogenic toxins or biological response modifiers (BRMs) into the portal system (liver damage) or systemic circulation with antibody formation (neurological conditions). Specifically, such hepato/biliary system disorders as primary biliary cirrhosis, primary sclerosing cholangitis, fatty liver of unknown aetiology, or cryptogenic cirrhosis, may be secondary to chronic pathogen carrier state in the intestine.

The links between the intestine and joint disease are also recognised. Joint diseases such as rheumatoid arthritis, the non-rheumatoid arthritidies including, ankylosing spondylitis, and Reiter's syndrome, may also be causally related to a chronic intestinal carrier state, as may other syndromes with an immune mediated component such as glomerulonephritis, haemolytic uraemic syndrome, juvenile diabetes mellitus, Behcet's syndrome, coeliac disease and dermatitis herpetiformis. Similarly, syndromes with an immune complex mediated component, such as scleroderma, systemic lupus erythematosus, mixed cryoglobulinaemia, polyarteritis, familial Mediterranean fever, amyloidosis, and the various presentations of such syndromes, together with such "idiopathic" states as chronic urticaria, may be manifestations of variations of immune regulated responses to related bowel-origin pathogens chronically shedding their antigen(s), toxins or biological response modifiers into the circulation. Other chronic conditions such as acne, and chronic idiopathic pseudo-obstructive syndrome, may well be influenced by similar mechanisms.

For many of these syndromes present therapy offers only palliation of symptoms and/or the induction of remission of the disease process but not cure. The present inventor therefore recognised the need to find a curative therapy for these wide ranging disease processes associated with considerable morbidity.

By judicious selection of the microorganisms of the invention it has been surprisingly found by the present inventor that lasting decolonization of the gut microflora does not require pretreatment to remove a portion of the host's existing enteric microflora. Thus, by incorporation of *Clostridia* spp. in the therapy, it has been surprisingly found that the prior art requirement for removal of at least a portion of the existing enteric microflora before administration of the substitute microflora is rendered unnecessary. Without the addition specifically of *Clostridia* species, the use of probiotic mixtures, e.g. such as those of *Bacteroides* and *Escherichia coli* failed to have the necessary impact on the above-mentioned clinical disorders for the treatment to be clinically useful. It required a prior purging of the gut of its presumably infected and abnormal bowel flora, re colonization with *bacteroides* and *Escherichia coli*—the main components of lower intestinal tract, and ongoing feeding of patients with such bacteria until colonization was established. The use of *Clostridia* appears to be the mainstay of this new therapy and the *Clostridia* appear to have power of themselves to remove offending bacterial species which may be responsible for the underlying condition (presumably pathogenic *clostridia*—yet to be identified scientifically). Hence, the combination of non-pathogenic *clostridia* together with the crucial major colonic bacterial components of *bacteroides* and *Escherichia coli* can now be used as oral therapy to crowd out/destroy/replace and recolonize the dysbiotic flora of patients with various gastrointestinal conditions which are caused by abnormal bowel flora. In fact, such a therapy becoming available has permitted or allowed greater understanding of the pathogenesis of many other conditions which hitherto were thought to be caused by degenerative, inflammatory, or auto immune mechanisms.

Thus according to a first embodiment of the invention there is provided a pharmaceutical composition useful for the treatment and/or prophylaxis of chronic disorders associated with the presence in the gastrointestinal tract of a mammalian host of abnormal or an abnormal distribution of microflora, which composition comprises viable non-pathogenic or attenuated pathogenic *Clostridia*.

Typically the composition includes *Clostridia* selected from the group consisting of *Clostridium absonum, Clostridium argentinense, Clostridium baratii, Clostridium bifermentans, Clostridium botulinum, Clostridium butyricum, Clostridium cadaveris, Clostridium carnis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii, Clostridium villosum*.

In a preferred form the composition further comprises one or more additional viable non-pathogenic or attenuated pathogenic microorganisms selected from the group consisting of *Bacteroides*, Eubacteria, Fusobacteria, Propionibacteria, *Lactobacilli*, anaerobic cocci, *Ruminococcus, Escherichia coli, Gemmiger, Desulfomonas, Peptostreptococcus* species and, more specifically, bacteria selected from Table 1. Preferably fungi are also present such as *Monilia*.

In a preferred form the composition comprises *Clostridia, Bacteroides, Peptostreptococcus, Escherichia coli, Bifidobacterium*, and *Lactobacillus*.

In a more preferred form the composition comprises *Clostridium innocuum, Clostridium bifermentans, Clostridium butyricum, Bacteroides fragilis, Bacteroides thetaiotaomicron, Bacteroides uniformis*, one or more strains of *Escherichia coli*, and one or more strains of *Lactobacillus*.

Alternatively, in a preferred form the composition comprises *Clostridium bifermentans, Clostridium innocuum*, and *Clostridium butyricum* in combination one or more strains of *Escherichia coli*, one or more strains of *bacteroides* and *Peptostreptococcus productus*, According to a second embodiment of the invention there is provided a pharmaceutical composition useful for the treatment and/or prophylaxis of chronic disorders associated with the presence in the gastrointestinal tract of a mammalian host of abnormal or an abnormal distribution of microflora, which composition comprises viable non-pathogenic or attenuated pathogenic *Escherichia coli*, at least one strain of viable non-pathogenic or attenuated pathogenic *Bacteroides*, and at least one other viable non-pathogenic or attenuated pathogenic microorganism.

In a preferred form the other viable non-pathogenic or attenuated pathogenic microorganism is selected from the group consisting of *Clostridia, Peptostreptococcus, Bifidobacterium*, and *Lactobacillus*.

Typically the composition of the first or second embodiments of the invention is derived from disease screened fresh homologous faeces, equivalent freeze-dried and reconstituted faeces or a "synthetic" faecal composition. The fresh homologous faeces does not include an antibiotic resistant population.

Typically, the composition of the first or second embodiments of the invention is a synthetic faecal composition.

In a preferred form the synthetic faecal composition comprises a preparation of viable flora which preferably in proportional content, resembles normal healthy human faecal flora which does not include antibiotic resistant populations. Suitable microorganisms may be selected from the following: *Bacteroides*, Eubacteria, Fusobacteria, Propionibacteria, *Lactobacilli*, anaerobic cocci, *Ruminococcus, Escherichia coli, Gemmiger, Clostridium, Desulfomonas, Peptostreptococcus, Bifidobacterium*, species and, more specifically, bacteria selected from Table 1. Preferably fungi are also present such as *Monilia*.

In a preferred form the composition of the first or second embodiments of the invention comprises a liquid culture.

Preferably, the composition of the first or the second embodiments of the present invention is lyophilized, pulverized and powdered. It may then be infused, dissolved such as in saline, as an enema.

Alternatively the powder may be encapsulated as enteric-coated capsules for oral administration. These capsules may take the form of enteric-coated microcapsules. As a powder it can preferably be provided in a palatable form for reconstitution for drinking or for reconstitution as a food additive. The composition can be provided as a powder for sale in combination with a food or drink. Typically, the food or drink is a dairy-based product or a soy-based product. The invention therefore also includes a food or food supplement containing a composition according to the first or second embodiment. In a preferred form the food or food supplement contains enteric-coated microcapsules of the composition of the invention. In a preferred form the food is yogurt.

The powder may be reconstituted also to be infused via naso-duodenal infusion. The composition can be combined with other adjuvants such as antacids to dampen bacterial inactivation in the stomach., e.g. Mylanta, Mucaine, Gastrogel. Acid secretion in the stomach could also be pharmacologically suppressed using H2-antagonists or proton pump inhibitors. Typically, the H2-antagonist is ranitidine. Typically the proton pump inhibitor is omeprazole.

The composition of the first or second embodiments of the invention is therefore preferably in the form of:

an enema composition which can be reconstituted with an appropriate diluent, or
enteric-coated capsules, or
enteric-coated microcapsules, or
powder for reconstitution with an appropriate diluent for naso-enteric infusion or colonoscopic infusion, or
powder for reconstitution with appropriate diluent, flavoring and gastric acid suppression agent for oral ingestion, or
powder for reconstitution with food or drink, or
food or food supplement comprising enteric-coated microcapsules of the composition, powder, jelly, or liquid.

According to a third embodiment of the invention there is provided a method for the treatment and/or prophylaxis of a chronic disorder associated with the presence in the gastrointestinal tract of a mammalian host of abnormal or an abnormal distribution of microflora, which method comprises administering an effective amount of a composition according to the first or second embodiment of the invention.

In its preferred form the treatment should effect a cure of the symptoms of such disorders. The change of flora is preferably as "near-complete" as possible and the flora is replaced by viable organisms which will crowd out any remaining, original flora.

The method of the present invention is applicable to animals in general, in particular humans and economically significant domestic animals.

In the case of humans, the present invention encompasses methods of treatment of chronic disorders associated with the presence of abnormal enteric microflora. Such disorders include but are not limited to those conditions in the following categories:

gastro-intestinal disorders including irritable bowel syndrome or spastic colon, functional bowel disease (FBD), including constipation predominant FBD, pain predominant FBD, upper abdominal FBD, non-ulcer dyspepsia (NUD), gastro-oesophageal reflux, inflammatory bowel disease including Crohn's disease, ulcerative colitis, indeterminate colitis, collagenous colitis, microscopic colitis, chronic *Clostridium difficile* infection, pseudomembranous colitis, mucous colitis, antibiotic associated colitis, idiopathic or simple constipation, diverticular disease, AIDS enteropathy, small bowel bacterial overgrowth, coeliac disease, polyposis coli, colonic polyps, chronic idiopathic pseudo obstructive syndrome;
chronic gut infections with specific pathogens including bacteria, viruses, fungi and protozoa;
viral gastrointestinal disorders, including viral gastroenteritis, Norwalk viral gastroenteritis, rotavirus gastroenteritis, AIDS related gastroenteritis;
liver disorders such as primary biliary cirrhosis, primary sclerosing cholangitis, fatty liver or cryptogenic cirrhosis;
rheumatic disorders such as rheumatoid arthritis, non-rheumatoid arthritidies, non rheumatoid factor positive arthritis, ankylosing spondylitis, Lyme disease, and Reiter's syndrome;
immune mediated disorders such as glomerulonephritis, haemolytic uraemic syndrome, juvenile diabetes mellitus, mixed cryoglobulinaemia, polyarteritis, familial Mediterranean fever, amyloidosis, scleroderma, systemic lupus erythematosus, and Behcets syndrome;
autoimmune disorders including systemic lupus, idiopathic thrombocytopenic purpura, Sjogren's syndrome, haemolytic uremic syndrome or scleroderma;
neurological syndromes such as chronic fatigue syndrome, migraine, multiple sclerosis, amyotrophic lateral sclerosis, myasthenia gravis, Gillain-Barre syndrome, Parkinson's disease, Alzheimer's disease, Chronic Inflammatory Demyelinating Polyneuropathy, and other degenerative disorders;
psychiatric disorders including chronic depression, schizophrenia, psychotic disorders, manic depressive illness;
regressive disorders including Asperger's syndrome, Rett syndrome, attention deficit hyperactivity disorder (ADHD), and attention deficit disorder (ADD);
the regressive disorder, autism;
sudden infant death syndrome (SIDS), anorexia nervosa;
dermatological conditions such as, chronic urticaria, acne, dermatitis herpetiformis and vasculitic disorders.

The above disorders are all characterized by their response to treatment with the method of the present invention.

Typically the change in enteric flora comprises introduction of an array of predetermined flora into the gastro-intestinal system, and thus in a preferred form the method of treatment comprises substantially completely displacing pathogenic enteric flora in patients requiring such treatment.

Furthermore, in some of these disorders a short course of antibiotics prior to probiotic treatment may be preferred to rid tissue-invasive pathogens originating in the bowel lumen. For example, in Crohn's disease, anti-tuberculosis therapy may be required for six to twelve weeks before the bowel is cleared out and the flora content exchanged for a predetermined flora.

Typically the antibiotic is an anti-Clostridial antibiotic such as vancomycin, rifampicin, and nitroimidazole or chloramphenicol. Typically the nitroimidazole is metronidazole.

In a preferred form of the invention, the method of treatment or prophylaxis further includes administration of at least one acid suppressant prior to administering, or in co-administration with, the composition of the invention.

In a preferred form of the invention the method of treatment or prophylaxis further includes nasogastric and/or nasoduodenal washout prior to administering said composition. The introduction of the composition into the gastrointestinal system can be effected by enema or per-colonoscope, via intubation of the small bowel using for example a large bore catheter equipped with distal balloon to effect rapid passage down the jejunum, or via the oral route with enteric-coated capsules, including enteric-coated microcapsules, or via the oral route with a supplemented food or drink.

In a preferred form the supplemented food or drink is a dairy-based or soy-based product. Typically the supplemented food product is yogurt.

According to the method of the invention each dose of the composition is in the range of about $10^3$ cells to about $10^{13}$ cells. Preferably each dose is in the range of about $10^5$ cells to about $10^{11}$ cells. More preferably each dose is in the range of about $10^9$ cells to about $10^{11}$ cells. In a preferred form of the invention an initial treatment regimen consisting of about $10^{10}$ cells per dose is administered about 3 to 6 times per day for a period sufficient to stabilize the gut flora. According to the method of the invention the treatment regimen may then comprise a maintenance dose of about $10^{10}$ cells per day.

Furthermore the present invention also relates to the treatment of animals, in particular to the treatment of gastrointestinal disorders in economically important domestic animals, such as cattle, sheep, horses, pigs, goats etc. The method of the present invention has been found to be especially useful in the treatment of the various forms of necrotizing enterocolitis which can be a major problem in animal stocks.

Obviously in the treatment of animals the appropriate composition of microflora will vary according to the species being treated and the constituent normal flora known to inhabit the gut.

Thus the composition according to the invention would comprise, a preparation of viable flora which preferably in proportional content, resembles the normal healthy faecal flora of the species involved. The compositions may be prepared in any of the forms already described and administered accordingly.

Best Method of Performing the Invention

In the practice of the invention a synthetic faecal composition of predetermined flora in the form of a liquid or dry powdered culture of *Clostridia, Bacteroides, Peptostreptococcus, Escherichia coli, Bifidobacterium*, and *Lactobacillus*, which composition does not include antibiotic resistant populations, is prepared as a liquid culture. Typically the method of the invention is applicable to a patient suffering from a chronic disorder associated with the presence of abnormal microflora in the gastrointestinal tract such as irritable bowel syndrome.

In the practice of the invention a composition of predetermined flora in the form of a liquid culture of *Clostridia, Bacteroides, Peptostreptococcus, Escherichia coli, Bifidobacterium*, and *Lactobacillus* is ingested by the patient in an amount sufficient to replace and recolonize the dysbiotic flora of the gastrointestinal tract, and reverse the disease process. Alternatively fresh homologous faeces obtained from a disease screened donor are liquefied and mixed with unprocessed bran. The mixture is then homogenized anaerobically under $CO_2$ cover and infused into the patient per colonoscope.

Cure or remission of symptoms is then monitored subjectively and by assessment of stool frequency or other appropriate criteria.

Using liquid cultures of *Clostridia, Bacteroides, Peptostreptococcus, Escherichia coli, Bifidobacterium*, and *Lactobacillus* the inventor has achieved total reversal of colitis, irritable bowel syndrome and constipation.

As indicated in the method of treatment aspect of the invention, a preparatory course of appropriate antibiotics may be used. For example, Septrin for chronic yersiniasis, Metronidazole for ulcerative colitis, anti-TB therapy in Crohn's disease, or Vancomycin in chronic *Clostridium difficile* infestations.

TABLE 1

| % of flora " | Organism(s) |
|---|---|
| 11.8(0.90) | *Bacteroides fragilis* ss. *Vulgatus* |
| 9.9(0.83) | *Collinsella aerofaciens* |
| 8.9(0.78) | *Bacteroides fragilis* ss. *Thetaiotaomicron* |
| 6.6(0.68) | *Peptostreptococcus productus* II |
| 6.0(0.64) | *Parabacteroides distasonis* |
| 4.4(0.55) | *Fusobacterium prausnitzii* |
| 3.5(0.49) | *Coprococcus eutactus* |
| 3.0(0.45) | *Collinsella aerofaciens* |
| 2.8(0.44) | *Peptostreptococcus productus* |
| 2.7(0.43) | *Ruminococcus bromii* |
| 2.6(0.43) | *Bifidobacterium adolescentis* |
| 2.2(0.39) | *Gemmiger formicilis, Bifidobacterium longum* |
| 2.1(0.38) | *Eubacterium siraeum* |

TABLE 1-continued

| % of flora " | Organism(s) |
|---|---|
| 1.8(0.35) | *Ruminococcus torques* |
| 1.7(0.34) | *Eubacterium rectale* |
| 1.6(0.33) | *Eubacterium rectale* IV, *Eubacterium eligens* |
| 1.5(0.32) | *Bacteroides eggerthii* |
| 1.4(0.31) | *Clostridium leptum* |
| 1.3(0.29) | *Bacteroides fragilis* ss. A |
| 1.2(0.29) | *Eubacterium biforme* |
| 0.91(0.25) | *Bifidobacterium infantis* |
| 0.84(0.24) | *Eubacterium rectale* |
| 0.57(0.20) | *Coprococcus comes, Pseudoflavonifractor capillosus* |
| 0.50(0.18) | *Ruminococcus albus, Dorea formicigenerans, Eubacterium hallii, Eubacterium ventriosum* I, *Fusobacterium russii* |
| 0.43(0.17) | *Ruminococcus obeum, Eubacterium rectale, Clostridium ramosum, Lactobacillus leichmannii* |
| 0.36(0.16) | *Ruminococcus, Butyrivibrio crossotus* |
| 0.30(0.14) | *Acidaminococcus fermentans, Eubacterium ventriosum, Bacteroides fragilis* ss. *fragilis*; |
| 0.23(0.12) | *Coprococcus catus, Aerostipes hadrus, Eubacterium cylindroides, Eubacterium ruminantium, Staphylococcus epidermidis* |
| 0.17(0.10) | *Peptostreptococcus BL, Eubacterium limosum, Tissirella praeacuta, Bacteroides L, Fusobacterium mortiferum* I, *Fusobacterium naviforme, Clostridium innocuum, Clostridium ramosum, Propionibacterium acnes, Ruminococcus flavefaciens* |
| 0.10(0.08) | *Ruminococcus AT, Peptococcus AU-1; Bacteroides fragilis* ss. *ovatus, Bacteroides* -ss. d, *Bacteroides* -ss. f; *Bacteroides* L-1, *Bacteroides* L-5; *Fusobacterium nucleatum, Fusobacterium mortiferum, Escherichia coli, Gemella morbillorum* |
| 0.05(0.05) | *Finegoldia magnus, Peptococcus* G, -AU-2; *Streptococcus intermedius, Ruminococcus lactaris, Gemmiger, Coprococcus* BH, -CC; *Eubacterium tenue, Eubacterium ramulus, Clostridium clostridiiforme, Bacteroides coagulans, Prevotella oralis, Prevotella brevis, Prevotella ruminicola, Odoribacter splanchnicus, Desulfomonas pigra, Fusobacterium* H, *Lactobacillus* G, *Succinivibrio* A. |

[b] The percentage of the faecal population (the standard deviation of the estimate is given in parentheses).
The invention will now be further described with reference to the following non-limiting examples.

EXAMPLES

Formulations

The probiotic therapeutic agents may be prepared in liquid culture anaerobically or aerobically (depending on bacterium cultured) in pure form. Alternatively the probiotics may be cultured on solid media and scraped into a liquid carrier. The resulting product may be spray-dried into a powder form and encapsulated or combined with excipients to be delivered in sachets.

Combinations of *Clostridia, Escherichia coli, Bacteroides*, and *Peptostreptococcus* with or without *Lactobacilli*, Bifidobacteria and Eubacteria may be used in varying disorders.

Example No 1

43 Year Old Female

Patient with long standing constipation not responsive to high-dose fiber usage together with prokinetics and standard anti-constipation treatments, was treated with increasing doses of orally administered bacterial mix (mixture composition included *Clostridium innocuum, bifermentans, butyricum*, together with *Bacteroides fragilis*, thetaiotaomicron and uniformis. Three strains of *Escherichia coli* were also included, as was *Lactobacillus*). This was ingested twice daily in the first two weeks and then daily thereafter. The patient was not given any pre-treatment purgative nor any antibiotics. However, she did take Ranitidine (an acid suppressant) three hours prior to ingestion of the bacterial mix. Two weeks after commencing the treatment the patient's constipation—which would prevent her from defecating for up to four days—reversed to increased frequency with reduction of bloating. Initially, gas production increased and there was turbulence and gurgling in the abdomen but after four weeks of treatment the patient was defecating on a daily basis with no sensation of incomplete emptying and an almost total absence of bloating. Following the treatment she remained virtually normal, defecating on a daily basis with 3 month follow up.

Example No 2

4$^1$Λ Year Old Male

Patient with 3 year history of diagnosis of autism associated with Irritable Bowel Syndrome characterized by constipation alternating with diarrhea and flatulence, with foul motions, was treated with oral administration of bacterial mix consisting of *Clostridium bifermentans, Clostridium innocuum*, and *Clostridium butyricum* in combination with three strains of *Escherichia coli*, three strains of *bacteroides* and *Peptostreptococcus* productus. These were ingested following acid suppression with Ranitidine and were at first taken 3 times daily, reducing to twice daily and then once daily maintenance for eight weeks. The patient's autistic symptoms were reversed quite dramatically with word power increasing from 20 to 200 words (counted by teacher at special 'autistic' school), he began to sleep through the night, and his IBS-type symptoms reverted to near-normality with less constipation, less diarrhea and less foul flatulence. He developed eye contact, was able to speak sentences up to six words constructed to commands and he began to look, to the untrained eye, as a relatively normal child by about week 10.

Example 3

Male Child, 5V_Years Old

Male child, 5½ years of age with autism symptoms dating back to age of around 15 months—but diagnosed significantly later. The patient presented initially with gastrointestinal symptoms in association with classical autism—for treatment of the bowel symptoms. Although stool test did not indicate any specific pathogen the bowel symptoms resembled those of a chronic infection or adult Irritable Bowel Syndrome (IBS), i.e. intermittent diarrhea, constipation, cramping, colicky pain, inability to sleep at night, occasional explosive diarrhea and incontinence. The patient was treated with orthostatic lavage using sodium pico-sulfate followed by water to produce voluminous diarrhea and to flush out the enteric contents. He was then given 125 mg Vancomycin three times daily orally followed by oral re-colonization with bacteria at a concentration of $10^9$ through to $10^{10}$, suspended in yoghurt—of strains which included *bacteroides, Escherichia coli*, and non-pathogenic *Clostridia*—including *Clostridium innocuum, bifermentans* and *ramosum*. The response was quite noticeable, in the reversal of the abnormal stool function towards normality. The patient was also able to sleep through the night without any explosive diarrhea and produced formed stools within five days of commencing the bacterial therapy. While the bacteriotherapy was continued the bowel symptoms were well controlled. Within 3-4 weeks of missing out the treatment for a week or two some of the symptoms would begin to recur. This suggested that the abnormal bacterial flora was suppressed rather than being cured with this treatment in this patient. The unexpected finding however, was a noticeable and marked reversal of symptoms of autism. Whereas previously repetitive movements were present with lack of eye contact, eye contact returned fairly rapidly together with cessation of repetitive movement and progressive increase of word power from around 20 words to around 600 words by the sixth month of treatment. The therapy continues now for more than 12 months with sustained reversal of autism and IBS symptoms.

Example 4

Male Child, 7 Years Old

A seven year old male patient was referred for treatment initially of bowel problems. He had developed autism between age 1 and 2 years characterized by lack of eye contact, repetitive movements, poorly developed cognitive abilities, vocabulary of fewer than 20 words The marked bowel symptoms were characterized by either constipation or large voluminous motions, sometimes diarrhea and explosive stools. Stool examination was negative.

The patient was given a pre-treatment of Vancomycin 125 mg twice daily and at one week he was given an orthostatic lavage consisting of picosulfate preparation which flushed out his bowel. He was then given twice daily oral bacteriotherapy consisting of cultures containing living probiotics. These included several *bacteroides* species, *Escherichia coli* and non-pathogenic *Clostridia* such as *Clostridium butyricum, Clostridium bifermentans* and *Clostridium innocuum*. Within two weeks the bowel symptoms reversed to normal defecation with soft, formed stool—once or twice per day. Constipation disappeared, eye contact returned over the next six weeks and vocabulary and word use quite dramatically improved, to everyone's surprise. When followed for eight months over 600 words could be counted in the vocabulary with sentences of up to eight words being constructed where previously this was not possible. Some abstract thinking was noted by teachers at the special autism school. Parents in particular noted reduced aggression, greater co-operation, and general increasing ability to develop a more normal relationship with the child. Repetitive action also disappeared.

Example 5

Male Child, 6 Years Old

A male patient aged 6 was referred to the clinic for treatment of chronic diarrhea and at times incontinence. The child had been autistic since the age of one year and three months. The diagnosis however was delayed. He had slow cognitive development and very limited vocabulary. There was virtually absent eye contact and at times violent and explosive behavior. The greatest problem with management was that of control of defecation as the child developed a fascination with the stools which would then be spread over furniture and walls. This brought severe pressure upon the family with respect to difficulty with management. Stool test was collected and again was negative for any pathogen. The patient was given Vancomycin 250 mg twice daily for 10 days after which a polyethylene glycol orthostatic lavage achieved a large volume flush of the bowel. He was then given twice daily oral bacteriotherapy in a neutral yogurt as a carrier.

Within one week the bowel function returned to virtual normality. However, the behavioral changes were just as rapid in reversing again characterized by fairly rapid reduction in aggressiveness and uncontrollable behavior, sleeping through the night, increased eye contact, and progressively increased word power. The behavior of spreading stools also disappeared, more as a behavioral change than learnt phenomenon. The patient was continued on medications for over a year and progressively improved in all parameters—at times fluctuating in severity.

What is claimed is:

1. A method for the treatment of a chronic gastrointestinal infection associated with an irritable bowel syndrome (IBS), a diarrhea, an alternating constipation/diarrhea, a flatulence, or a constipation in a gastrointestinal tract of a mammal, which method comprises:
   (a) providing a pharmaceutical composition comprising:
       (1) a plurality of viable non-pathogenic *Clostridia* spores; and
       (2) a plurality of viable non-pathogenic *Collinsella*,
   wherein the viable non-pathogenic *Clostridia* is selected from the group consisting of: *Clostridium bifermentans*, *Clostridium butyricum*, *Clostridium difficile*, *Clostridium ramosum*, *Clostridium innocuum*, and a combination thereof; and
   (b) administering to the mammal an effective amount of the pharmaceutical composition of (a).

2. The method of claim 1, further comprising a viable non-pathogenic *Clostridia* in the form of a spore selected from the group consisting of a *Clostridium absonum*, *Clostridium argentinense*, *Clostridium baratii*, *Clostridium bifermentans*, *Clostridium botulinum*, *Clostridium butyricum*, *Clostridium cadaveris*, *Clostridium camis*, *Clostridium celatum*, *Clostridium chauvoei*, *Clostridium clostridioforme*, *Clostridium cochlearium*, *Clostridium difficile*, *Clostridium fallax*, *Clostridium felsineum*, *Clostridium ghonii*, *Clostridium glycolicum*, *Clostridium haemolyticum*, *Clostridium hastiforme*, *Clostridium histolyticum*, *Clostridium indolis*, *Clostridium innocuum*, *Clostridium irregulare*, *Clostridium limosum*, *Clostridium malenominatum*, *Clostridium novyi*, *Clostridium oroticum*, *Clostridium paraputrificum*, *Clostridium perfringens*, *Clostridium piliforme*, *Clostridium putrefaciens*, *Clostridium putrificum*, *Clostridium ramosum*, *Clostridium sardiniense*, *Clostridium sartagoforme*, *Clostridium scindens*, *Clostridium septicum*, *Clostridium sordellii*, *Clostridium sphenoides*, *Clostridium spiroforme*, *Clostridium sporogenes*, *Clostridium subterminale*, *Clostridium symbiosum*, *Clostridium tertium*, *Clostridium tetani*, *Clostridium welchii*, and a *Clostridium villosum*.

3. The method of claim 1, wherein
   (a) the pharmaceutical composition is lyophilized, pulverized and powdered or a liquid culture;
   (b) the pharmaceutical composition is formulated as or is administered in a form selected from the group consisting of an enteric coated capsule, an enteric coated microcapsule, a reconstituted powder, an enema, a food, a food supplement, or a drink; or
   (c) the method of (b), wherein the food comprises a yogurt, a dairy-based product, a soy-based product, or a derivative thereof.

4. The method of claim 1, wherein the mammal is a human.

5. The method of claim 1, wherein:
   (a) the method further comprises administration of an effective amount of at least one antibiotic prior to administering the pharmaceutical composition;
   (b) the method of (a), wherein the antibiotic comprises an anti-Clostridial antibiotic; or
   (c) the method of (b), wherein the anti-Clostridial antibiotic is selected from the group consisting of a vancomycin, a rifampicin and a nitroimidazole.

6. The method of claim 1, wherein:
   (a) the method further comprises a nasogastric or a nasoduodenal washout prior to administering the pharmaceutical composition; or
   (b) the administering is by one or more routes selected from the group consisting of ingestion, enteral infusion, enema, per-colonoscope, intubation of the small bowel and orally.

7. The method of claim 1, wherein the chronic gastrointestinal disorder is a *Clostridium difficile* infection.

8. The method of claim 1, comprising a treatment regimen:
   of about $10^{10}$ *Clostridia* cells per dose administered about 3 to 6 times per day for a period sufficient to stabilize the gut flora; or,
   comprising a unit dose of viable non-pathogenic *Clostridia* in the range of between about $10^3$ cells to about $10^{13}$ cells; or between about $10^5$ cells to about $10^{11}$ cells, or between about $10^9$ cells to about $10^{11}$ cells.

9. The method of claim 1, further comprising administering at least one strain of a viable non-pathogenic *Bacteroides*.

10. The method of claim 1, further comprising administering at least one viable non-pathogenic bacteria selected from the group consisting of: a *Bacteroides caccae*, a Pseudoflavonifractor *capillosus*, a *Bacteroides coagulans*, a Parabacteroides *distasonis*, a *Bacteroides eggerthii*, a *Bacteroides forsythus*, *Bacteroides fragilis*, a *Bacteroides gracilis*, a *Bacteroides levil*, a *Bacteroides macacae*, a *Bacteroides merdae*, a *Bacteroides ovatus*, a *Bacteroides pneumosintes*, a *Bacteroides putredinis*, a *Bacteroides pyogenes*, an *Odoribacter splanchnicus*, a *Bacteroides stercoris*, a *Bacteroides tectum*, a *Bacteroides thetaiotaomicron*, a *Bacteroides uniformis*, a *Bacteroides ureolyticus*, a *Bacteroides vulgatus*, and a combination thereof.

11. The method of claim 1, further comprising administering one or more additional viable non-pathogenic anaerobic cocci.

12. The method of claim 1, further comprising administering one or more additional viable non-pathogenic microorganisms in the form of a spore or spores, wherein the one or more additional viable non-pathogenic microorganism comprises one or more viable non-pathogenic bacteria selected from the group consisting of a *Bacteroides*, a *Collinsella*, a Fusobacteria, a Propionibacteria, a *Lactobacilli*, an anaerobic cocci, a *Ruminococcus*, a Gemmiger, a Desulfomonas, a *Peptostreptococcus* species and a combination thereof.

13. The method of claim 1, wherein the pharmaceutical composition comprises:
   (a) a *Clostridium innocuum*, a *Clostridium bifermentans*, a *Clostridium butyricum*, a *Bacteroides fragilis*, a *Bacteroides thetaiotaomicron*, a *Bacteroides uniformis*, one or more strains of an *Escherichia coli*, and one or more strains of a *Lactobacillus*; or,
   (b) a *Clostridium bifermentans*, a *Clostridium innocuum*, and a *Clostridium butyricum* in combination with one or more strains of an *Escherichia coli*, one or more strains of a *Bacteroides* and a *Peptostreptococcus productus*.

14. A method for the treatment of a *Clostridium difficile* infection in a gastrointestinal tract of a mammalian host, which method comprises:
   (a) providing a pharmaceutical composition comprising a plurality of viable non-pathogenic *Clostridia* spores and non-pathogenic viable *Coffinsella*; and (b) administering to the mammalian host an effective amount of the pharmaceutical composition of (a).

15. The method of claim 1, further comprising:
(a) one or more additional viable non-pathogenic microorganisms selected from the group consisting of a *Bacteroides fragilis* ss. *Vulgatus*, *Collinsella aerofaciens*, *Bacteroides fragilis* ss. *Thetaiotaomicron*, *Peptostreptococcus productus* II, *Parabacteroides distasonis Fusobacterium prausnitzii*, *Coprococcus eutactus*, *Collinsella aerofaciens* III, *Peptostreptococcus productus* I, *Ruminococcus bromii*, *Bifidobacterium adolescentis*, *Gemmiger formicilis*, *Bifidobacterium longum*, *Eubacterium siraeum*, *Ruminococcus torques*, *Eubacterium rectale*, *Eubacterium eligens*, *Bacteroides eggerthii*, *Clostridium leptum*, *Bacteroides fragilis* ss. A, *Eubacterium biforme*, *Bifidobacterium infantis*, *Eubacterium rectale* III-F, *Coprococcus comes*, *Pseudoflavonifractor capillosus*, *Ruminococcus albus*, *Dorea formicigenerans*, *Eubacterium haffii*, *Eubacterium ventriosum* I, *Fusobacterium russi*, *Ruminococcus obeum*, *Eubacterium rectale*, *Clostridium ramosum*, *Lactobacillus leichmannii*, *Ruminococcus callidus*, *Butyrivibrio crossotus*, *Acidaminococcus fermentans*, *Eubacterium ventriosum*, *Bacteroides fragilis* ss. *fragilis*, *Bacteroides* AR, *Coprococcus catus*, *Aerostipes hadrus*, *Eubacterium cylindroides*, *Eubacterium ruminantium*, *Eubacterium* CH-1, *Staphylococcus epidermidis*, *Peptostreptococcus* BL, *Eubacterium limosum*, *Tissirella praeacuta*, *Bacteroides* L, *Fusobacterium mortiferum* I, *Fusobacterium naviforme*, *Clostridium innocuum*, *Clostridium ramosum*, *Propionibacterium acnes*, *Ruminococcus flavefaciens*, *Ruminococcus* AT, *Peptococcus* AU-1, *Bacteroides fragilis* ss. *ovatus*, -ss. d, -ss. f; *Bacteroides* L-1, L-5; *Fusobacterium nucleatum*, *Fusobacterium mortiferum*, *Escherichia coli*, *Gemella morbillorum*, *Finegoldia magnus*, *Peptococcus* G, -AU-2; *Streptococcus intermedius*, *Ruminococcus lactaris*, *Ruminococcus* CO *Gemmiger* X, *Coprococcus* BH, —CC; *Eubacterium tenue*, *Eubacterium ramulus*, *Bacteroides clostridliformis* ss. *clostridliformis*, *Bacteroides coagulans*, *Prevotella oralis*, *Prevotella ruminicola*, *Odoribacter splanchnicus*, *Desuifomonas pigra*, *Lactobacillus* G, *Succinivibrio* A, and a combination thereof;
(b) one or more additional viable non-pathogenic fungi, wherein optionally the fungi comprises a *Monilia*; or
(c) one or more additional viable non-pathogenic *Bifidobacterium*.

16. The method of claim 1, wherein the plurality of viable non-pathogenic *Collinsella* comprises a plurality of viable non-pathogenic *Collinsella* spores.

17. The method of claim 1, wherein the method comprises providing a pharmaceutical composition consisting essentially of:
(1) a plurality of viable non-pathogenic *Clostridia* spores; and
(2) a plurality of viable non-pathogenic *Collinsella* spores.

18. The method of claim 14, wherein the plurality of viable non-pathogenic *Collinsella* comprises a plurality of viable non-pathogenic *Collinsella* spores.

19. The method of claim 14, wherein the method comprises providing a pharmaceutical composition consisting essentially of: a plurality of viable non-pathogenic *Clostridia* spores and viable non-pathogenic *Collinsella* spores.

* * * * *

UNITED STATES PATENT AND TRADEMARK OFFICE
CERTIFICATE OF CORRECTION

PATENT NO. : 9,050,358 B2  Page 1 of 1
APPLICATION NO. : 14/270034
DATED : June 9, 2015
INVENTOR(S) : Thomas Julius Borody It is certified that error appears in the above-identified patent and that said Letters Patent is hereby corrected as shown below:

Claims

Column 14, Line 67, claim 14, delete "Coffinsella" and please insert -- "Collinsella" --.

Signed and Sealed this
Twenty-ninth Day of March, 2016

Michelle K. Lee
*Director of the United States Patent and Trademark Office*